United States Patent [19]

Gurien et al.

[11] 4,193,923

[45] Mar. 18, 1980

[54] TETRAHYDRO 2-CARBAZOLYL METHYL MALONATE DERIVATIVES

[75] Inventors: Harvey Gurien, West Orange; Sidney Teitel, Clifton, both of N.J.

[73] Assignee: Hoffmann-La Roche Inc., Nutley, N.J.

[21] Appl. No.: 23,114

[22] Filed: Mar. 23, 1979

Related U.S. Application Data

[62] Division of Ser. No. 935,197, Aug. 21, 1978.

[51] Int. Cl.$^2$ ................... C07D 209/82; C07D 209/86
[52] U.S. Cl. ...................................... 260/315; 424/274
[58] Field of Search .......................................... 260/315

[56] References Cited

U.S. PATENT DOCUMENTS 3,896,145 7/1975 Berger et al. .................... 260/315

*Primary Examiner*—John D. Randolph
*Assistant Examiner*—R. W. Ramsuer
*Attorney, Agent, or Firm*—Jon S. Saxe; George M. Gould; William G. Isgro

[57] ABSTRACT

A process for the preparation of α-methyl-carbazole-2-acetic acids, which comprises reacting an α-methyl-3-oxocyclohexane malonic acid di-lower alkyl ester with a substituted phenylhydrazine, and thereafter sequentially oxidizing and hydrolyzing the reaction product to obtain the desired acid, is described.

2 Claims, No Drawings

TETRAHYDRO 2-CARBAZOLYL METHYL MALONATE DERIVATIVES

This is a division of application Ser. No. 935,197 filed Aug. 21, 1978.

BRIEF SUMMARY OF THE INVENTION

The invention relates to a process for the preparation of a compound of the formula

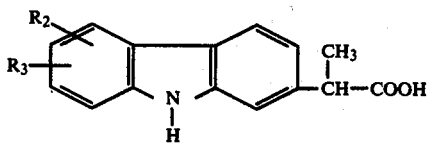

wherein $R_2$ is hydrogen, halogen, trifluoromethyl, hydroxy, lower alkyl, hydroxy-lower alkyl, lower alkylthio, amino, mono-lower alkylamino, or di-lower alkylamino; and $R_3$ is halogen, trifluoromethyl, lower alkyl, hydroxy-lower alkyl, lower alkoxy, lower alkylthio, hydroxy, amino, mono-lower alkylamino or di-lower alkylamino, or $R_2$, taken together with an adjacent $R_3$, is also lower alkylenedioxy, which comprises treating an α-methyl-3-oxocyclohexane malonic acid di-lower alkyl ester with a phenylhydrazine of the formula

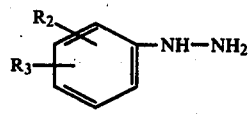

wherein $R_2$ and $R_3$ are as previously described, to yield a compound of the formula

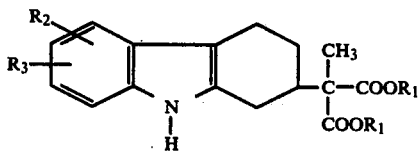

wherein $R_1$ is lower alkyl, and $R_2$ and $R_3$ are as previously described, treating the compound of formula IV with an oxidizing agent such as chloranil, to yield a compound of the formula

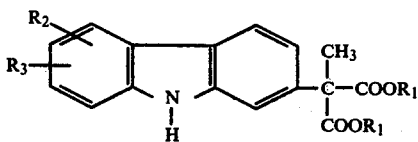

wherein $R_1$, $R_2$ and $R_3$ are as previously described, and treating the resulting compound of formula V to obtain the desired α-methyl-carbazole-2-acetic acid of formula I.

DETAILED DESCRIPTION OF THE INVENTION

As used herein, the term "lower alkyl" denotes a straight or branched chain hydrocarbon group containing 1-7 carbon atoms, for example, methyl, ethyl, propyl, isopropyl, butyl, isobutyl, tertiary butyl, neopentyl, pentyl, heptyl, and the like. The term "lower alkoxy" denotes an alkyloxy group in which the alkyl group is as described above, for example, methoxy, ethoxy, propoxy, isopropoxy, butoxy, pentoxy, and the like. The term "lower alkylthio" denotes an alkyl thioether group in which the alkyl group is as described above, for example, methylthio, ethylthio, propylthio, isopropylthio, butylthio, pentylthio, and the like. The term "halogen" denotes all the halogens, that is, bromine, chlorine, fluorine and iodine; bromine and chlorine are preferred. The term "lower alkylene" denotes a straight or branched chain alkylene of 1–7 carbon atoms, for example, methylene, ethylene, propylene, butylene, methylmethylene and the like. The term "lower alkylenedioxy" preferably denotes methylenedioxy and the like.

Exemplary of mono-lower alkylamino are methylamino, ethylamino and the like. Exemplary of di-lower alkylamino are dimethylamino, diethylamino and the like. Exemplary of amino-lower alkoxy are aminomethoxy, aminoethoxy and the like.

The compounds of the formula

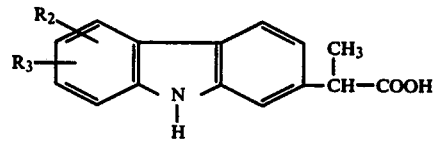

wherein $R_2$ is hydrogen, halogen, trifluoromethyl, hydroxy, lower alkyl, hydroxy-lower alkyl, lower alkylthio, amino, mono-lower alkylamino, or di-lower alkylamino; and $R_3$ is halogen, trifluoromethyl, lower alkyl, hydroxy-lower alkyl, lower alkoxy, lower alkylthio, hydroxy, amino, mono-lower alkylamino or di-lower alkylamino, or $R_2$, taken together with an adjacent $R_3$ is also lower alkylenedioxy, are useful as anti-inflammatory, analgesic and anti-rheumatic agents.

The process of the invention comprises the preparation of the compounds of formula I. More specifically, an α-methyl-3-oxocyclohexane malonic acid di-lower alkyl ester of the formula

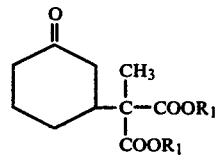

wherein $R_1$ is lower alkyl, is treated with a phenylhydrazine of the formula

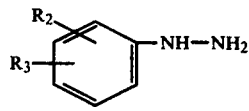

wherein $R_2$ and $R_3$ are as previously described.

This reaction is carried out in the presence of an inert organic solvent, for example, an alkanol such as methanol, ethanol, propanol, or the like. The reaction yields a compound of the formula

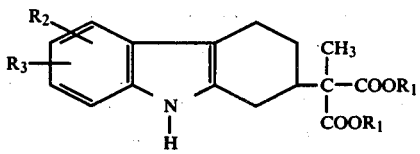

wherein $R_1$, $R_2$ and $R_3$ are as previously described. The foregoing reaction can be conveniently carried out at room temperature or above, for example, at a temperature in the range of 25° to about 100° C. The compound of formula IV can be recovered, if desired, utilizing conventional methods. However, it is also possible to utilize the reaction product in situ in the next step of the process of the invention.

Exemplary of the compounds of formula IV are:
dimethyl-[6-chloro-1,2,3,4-tetrahydro-2-carbazolyl]-methyl malonate;
diethyl-[6-chloro-1,2,3,4-tetrahydro-2-carbazolyl]-methyl malonate;
dipropyl-[6-chloro-1,2,3,4-tetrahydro-2-carbazolyl]-methyl malonate;
dibutyl-[6-chloro-1,2,3,4-tetrahydro-2-carbazolyl]-methyl malonate;
diethyl-[6-methyl-1,2,3,4-tetrahydro-2-carbazolyl]-methyl malonate;
diethyl-[6-trifluoromethyl-1,2,3,4-tetrahydro-2-carbazolyl]-methyl malonate;
diethyl-[6-hydroxy-1,2,3,4-tetrahydro-2-carbazolyl]-methyl malonate;
diethyl-[6-ethyl-1,2,3,4-tetrahydro-2-carbazolyl]-methyl malonate;
diethyl-[6-propyl-1,2,3,4-tetrahydro-2-carbazolyl]-methyl malonate;
diethyl-[6-hydroxymethyl-1,2,3,4-tetrahydro-2-carbazolyl]-methyl malonate;
diethyl-[6-methylthio-1,2,3,4-tetrahydro-2-carbazolyl]-methyl malonate;
diethyl-[6-amino-1,2,3,4-tetrahydro-2-carbazolyl]-methyl malonate;
diethyl-[6-methylamino-1,2,3,4-tetrahydro-2-carbazolyl]-methyl malonate;
diethyl-[6-dimethylamino-1,2,3,4-tetrahydro-2-carbazolyl]-methyl malonate;
diethyl-[5-chloro-1,2,3,4-tetrahydro-2-carbazolyl]-methyl malonate;
diethyl-[7-chloro-1,2,3,4-tetrahydro-2-carbazolyl]-methyl malonate; and
diethyl-[8-chloro-1,2,3,4-tetrahydro-2-carbazolyl]-methyl malonate;

Exemplary of the compounds of formula II are:
α-methyl-3-oxocyclohexane malonic acid dimethyl ester;
α-methyl-3-oxocyclohexane malonic acid diethyl ester;
α-methyl-3-oxocyclohexane malonic acid dipropyl ester;
α-methyl-3-oxocyclohexane malonic acid dibutyl ester;
α-methyl-3-oxocyclohexane malonic acid dipentyl ester; and the like.

Exemplary of the substituted phenylhydrazines of formula III are:
p-chlorophenylhydrazine;
p-trifluoromethylphenylhydrazine;
p-hydroxyphenylhydrazine;
p-methylphenylhydrazine;
p-ethylphenylhydrazine;
p-hydroxymethylphenylhydrazine;
p-methylthiophenylhydrazine;
p-aminophenylhydrazine;
p-mono-methylaminophenylhydrazine;
p-dimethylaminophenylhydrazine;
m-chlorophenylhydrazine;
m-trifluoromethylphenylhydrazine;
m-hydroxyphenylhydrazine;
m-methylphenylhydrazine;
m-ethylphenylhydrazine;
m-hydroxymethylphenylhydrazine;
m-methylthiophenylhydrazine;
m-aminophenylhydrazine;
m-mono-methylaminophenylhydrazine; and
m-dimethylaminophenylhydrazine.

The reaction product of formula IV is treated with an oxidizing agent in a hydrocarbon solvent such as benzene, toluene, xylene, and the like, to yield a compound of the formula

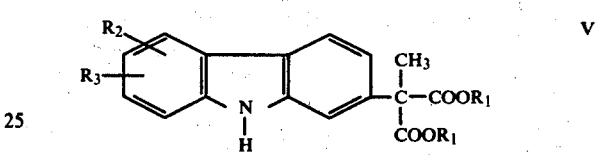

wherein $R_1$, $R_2$ and $R_3$ are as previously described.

Exemplary of the oxiding agents are paraquinones such as paraquinone, chloranil (tetramethyl-p-quinone), dichloroparaquinone, and dicyanoparaquinone. The reaction can be carried out at room temperature at the reflux temperature of the reaction mixture. Preferably, the reaction is carried out at the reflux temperature of the reaction mixture.

The compound of formula V can be recovered utilizing conventional methods, for example, crystallization or the like. Exemplary of the reaction products of formula V are:
dimethyl-[6-chloro-2-carbazolyl]-methyl malonate;
diethyl-[6-chloro-2-carbazolyl]-methyl malonate;
dipropyl-[6-chloro-2-carbazolyl]-methyl malonate;
dibutyl-[6-chloro-2-carbazolyl]-methyl malonate;
diethyl-[6-methyl-2-carbazolyl]-methyl malonate;
diethyl-[6-trifluoromethyl-2-carbazolyl]-methyl malonate;
diethyl-[6-hydroxy-2-carbazolyl]-methyl malonate;
diethyl-[6-ethyl-2-carbazolyl]-methyl malonate;
diethyl-[6-propyl-2-carbazolyl]-methyl malonate;
diethyl-[6-hydroxymethyl-2-carbazolyl]-methyl malonate;
diethyl-[6-methylthio-2-carbazolyl]-methyl malonate;
diethyl-[6-amino-2-carbazolyl]-methyl malonate;
diethyl-[6-methylamino-2-carbazolyl]-methyl malonate;
diethyl-[6-dimethylamino-2-carbazolyl]-methyl malonate;
diethyl-[5-chloro-2-carbazolyl]-methyl malonate;
diethyl-[7-chloro-2-carbazolyl]-methyl malonate; and
diethyl-[8-chloro-2-carbazolyl]-methyl malonate.

The compounds of formula V are then hydrolyzed to yield α-methylcarbazole-2-acetic acids of formula I. The hydrolysis can be carried out, for example, utilizing glacial acetic acid in the presence of a hydrohalic acid such as hydrochloric acid. The resulting end product of formula I is recovered utilizing conventional methods. As already mentioned, the compounds of formula I are useful as analgesic, anti-inflammatory and anti-rheumatic agents.

The following Examples further illustrate the invention. All temperatures are in degrees Centigrade, unless otherwise mentioned.

EXAMPLE 1

Preparation of α-methyl-3-oxocyclohexane malonic acid diethyl ester

Into a 2 l. 3-neck flask equipped with stirrer, condenser, thermometer, dropping funnel, and under a nitrogen atmosphere is placed 325 ml. of ethanol, and 2.5 g. of freshly cut sodium is added. When solution of the sodium is effected, 200 g. of diethyl methyl malonate is added in 5 minutes, and the mixture is stirred at room temperature for 1 hour. At the end of this period a solution of 100 g. of 2-cyclohexen-1-one in 130 ml. of ethanol is added through the dropping funnel over a period of 1 hour. The ensuing mild exothermic reaction causes the temperature to rise to 42°. Stirring is continued overnight at room temperature, after which 20 ml. of acetic acid is added, and the mixture is evaporated at reduced pressure. The residual oil is dissolved in 1.31 l. of ether, transferred to a separatory funnel and washed with three 230 ml. portions of water. The ether solution is dried over anhydrous sodium sulfate, filtered, and dried over anhydrous calcium sulfate. The ether is removed at reduced pressue and the residual oil distilled under high vacuum using a 6-inch Vigreux column. After removal of a forerun of 22.5 g., bp 49°–129°/0.14–0.21 mm, α-methyl-3-oxocyclohexane malonic acid diethyl ester distills at 129°–130°/0.2 mm; 211.5 g, 75.4% of theory.

EXAMPLE 2

Preparation of diethyl-[6-chloro-1,2,3,4-tetrahydro-2-carbazolyl]-methyl malonate Into a 1 l. 3-neck flask equipped with stirrer, condenser, thermometer, and under nitrogen atmosphere is placed 100 g. of α-methyl-3-oxocyclohexane malonic acid diethyl ester, 66.3 g. of p-chlorophenylhydrazine hydrochloride and 300 ml. of ethanol. The suspension is stirred at room temperature for 1.5 hours, and is then refluxed for 1.5 hours. The hot reaction mixture containing some insolubles is allowed to cool to room temperature overnight without stirring. It is then cooled in an ice bath, and the crystals filtered. Residual material in the flask is washed onto the funnel with the mother liquor, the presscake sucked dry, washed with three 50 ml. portions of ice cold ethanol, then with 50 ml. of 1:1 hexane-ethanol, and dried at 40°–50° at reduced pressure. The resultant 97.1 g. of bluish-white solid is placed in a 1 l. 3-neck flask equipped with stirrer, under nitrogen atmosphere, surrounded by an ice bath, and is stirred 15 minutes with 500 ml. of cold water, filtered, washed with three 100 ml. portions of cold water and dried at 40° at reduced pressure to give 78.8 g. of diethyl-[6-chloro-1,2,3,4-tetrahydro-2-carbazolyl]methyl malonate, mp 129°–130°, 56.5% of theory.

Anal. Calcd. for $C_{20}H_{24}ClNO_4$: C, 63.57; H, 6.40; N, 3.71; Found: C, 63.59; H, 6.58; N, 3.84.

EXAMPLE 3

Preparation of diethyl-[6-chloro-2-carbazolyl]methyl malonate

Into a 3 l. 3-neck flask wrapped with aluminum foil, equipped with stirrer, condenser, thermometer, and under nitrogen atmosphere are placed 161.2 g. of diethyl-[6-chloro-1,2,3,4-tetrahydro-2-carbazolyl]methyl malonate, 251.0 g. of chloranil and 1.65 l. of xylene. The mixture is refluxed 6 hours and allowed to cool overnight. The supernatant liquid is decanted and filtered. The residue is triturated three times, each with 650 ml. of warm (45°–50°) benzene, and the supernatants are decanted and filtered. 2 L. of ether is added to the combined filtrates and the mixture extracted with four 650 ml. portions of 2 N sodium hydroxide. The organic phase is washed with water until the washings are neutral and is then dried over anhydrous magnesium sulfate. The organic phase is then evaporated at reduced pressure using a water aspirator. The residue is then dried at high vacuum. The resulting 156.3 g. of brown solid is dissolved in 300 ml. of boiling carbon tetrachloride, treated with 3.0 g. of charcoal, filtered hot, diluted with 600 ml. of hexane, heated to the boil, seeded immediately upon cessation of heating with crystals of diethyl-[6-chloro-2-carbazolyl]methyl malonate, allowed to cool overnight while stirring under a nitrogen atmosphere and then cooled in an ice bath. The crystalline material is filtered, and washed with three 100 ml. portions of 2:1 hexane-carbon tetrachloride. The solid, when dried at reduced pressure, yields 119.4 g. of diethyl-[6-chloro-2-carbazolyl]methyl malonate, mp 134°–135°, 75.2% of theory.

Anal. Calcd. for $C_{20}H_{20}ClNO_4$: C, 64.26; H, 5.39; N, 3.75; Found: C, 64.41; H, 5.49; N, 3.72.

EXAMPLE 4

Preparation of 6-chloro-α-methylcarbazole-2-acetic acid

Into a 5 l. 3-neck flask equipped with a stirrer, thermometer, condenser and nitrogen atmosphere is placed 247 g. of diethyl-[6-chloro-2-carbazolyl]methyl malonate, 1.9 l. of glacial acetic acid and 1.9 l. of 6 N hydrochloric acid. The mixture is stirred and refluxed overnight and the resulting black solution allowed to cool to room temperature. The solid formed is filtered, washed with three 200 ml. portions of 1:1 acetic acid-water, followed by four 300 ml. portions of water, and dried at reduced pressure. The crude 6-chloro-α-methylcarbazole-2-acetic acid (approximately 192 g.) is dissolved in 1.2 l. of cold (10°) 1 N potassium hydroxide, and the solution is extracted with four 300 ml. portions of ether, and then while cooling in an ice bath, under nitrogen, is acidified by the addition of 100 ml. of concentrated hydrochloric acid. Stirring is continued for 15 minutes, the precipitated solid is filtered, washed with three 100 ml. portions of water, and dried at reduced pressure to give 167.7 g. Final purification is achieved by crystallization from 4.7 l. of boiling 1,2-dichloroethane with 8.0 g. of charcoal. The amber solution is allowed to cool overnight. The crystals are filtered, washed with two 200 ml. portions of cold dichloroethane and dried at reduced pressure. The yield of almost white 6-chloro-α-methylcarbazole-2-acetic acid is 103.8 g., mp 198.5°–201°, 57.3% of theory.

We claim:

1. A compound of the formula

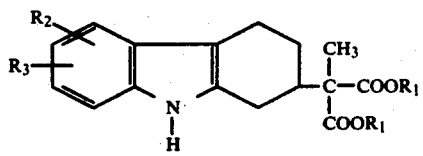

wherein $R_1$ is lower alkyl, $R_2$ is hydrogen, halogen, trifluoromethyl, hydroxy, lower alkyl, hydroxy-lower alkyl, lower alkylthio, amino, mono-lower alkylamino, or di-lower alkylamino; and $R_3$ is halogen, trifluoromethyl, lower alkyl, hydroxy-lower alkyl, lower alkoxy, lower alkylthio, hydroxy, amino, mono-lower alkylamino or di-lower alkylamino, or $R_2$, taken together with an adjacent $R_3$ is also alkylenedioxy.

2. A compound in accordance with claim 1, diethyl-[6-chloro-1,2,3,4-tetrahydro-2-carbazolyl]methyl malonate.

* * * * *